United States Patent [19]
Vo-Dinh

[11] Patent Number: 4,674,878
[45] Date of Patent: Jun. 23, 1987

[54] PRACTICAL SUBSTRATE AND APPARATUS FOR STATIC AND CONTINUOUS MONITORING BY SURFACE-ENHANCED RAMAN SPECTROSCOPY

[75] Inventor: Tuan Vo-Dinh, Knoxville, Tenn.

[73] Assignee: The United States of America as represented by the United States Department of Energy, Washington, D.C.

[21] Appl. No.: 732,317

[22] Filed: May 9, 1985

[51] Int. Cl.[4] ............................................. G01N 21/65
[52] U.S. Cl. ................................................... 356/301
[58] Field of Search ......................................... 356/301

[56] References Cited

PUBLICATIONS

Vo-Dinh et al., "Surface-Enhancee Raman Spectrometry for Trace Organic Analysis", Anal Chem 1984, 56 #9, Aug. 1984, pp. 1667-1670.

*Primary Examiner*—Vincent P. McGraw
*Attorney, Agent, or Firm*—Stephen D. Hamel; Judson R. Hightower

[57] ABSTRACT

A substrate for use in surface-enhanced Raman spectroscopy (SERS) is disclosed, comprising a support, preferably flexible, coated with roughness-imparting microbodies and a metallized overcoating. Also disclosed is apparatus for using the aforesaid substrate in continuous and static SERS trace analyses, especially of organic compounds.

19 Claims, 9 Drawing Figures

PRACTICAL SUBSTRATE AND APPARATUS FOR STATIC AND CONTINUOUS MONITORING BY SURFACE-ENHANCED RAMAN SPECTROSCOPY

BACKGROUND OF THE INVENTION

The present invention relates to a practical substrate, preferably flexible, for surface-enhanced Raman spectroscopy, and to an apparatus for using the substrate in trace analysis, particularly of organic compounds, in either a continuous or a static monitoring mode.

The U.S. government has rights in this invention pursuant to a contract awarded by the U.S. Department of Energy.

A number of optical spectroscopic techniques have been developed to characterize solid-gas (vacuum), solid-liquid (electrolyte) and solid-solid interfaces. In particular, the chemical identity of surface-adsorbed molecular species can be determined with specificity using surface analysis spectroscopy (SAS), such as infrared transmission spectroscopy and electron energy loss spectroscopy, instead of surface electronic absorption spectroscopy or photoacoustic spectroscopy. For example, SAS techniques can be used in the analysis of molecules sorbed at the surface of an electrode within a working electrochemical cell.

Among the SAS methods, surfce-enhanced Raman spectrometry (SERS) has recently received considerable attention. Enhancements by factors of $10^3$ to $10^6$ can be realized in the Raman scattering intensity for adsorbates on or near special rough metal surfaces. This phenomenon has been verified for adsorbates at silver, copper, and gold metal surfaces under both solution and vacuum conditions. See, e.g., Albrecht & Creighton, 99 J. AM. CHEM. SOC. 5215 (1977). These spectacular enhancement factors help overcome the normally low sensitivity of Raman spectroscopy which had often necessitated the use of powerful, costly laser sources for excitation.

In spite of the current interest in the SERS phenomenon, there has been no report on a generalized application of this effect for trace analysis. Most of the basic studies reported in the literature deal with samples of concentrations between $10^{-1}$ and $10^{-3}$M, well above the concentration range of interest to analytical spectroscopists. Also, previous SERS studies have involved only rigid substrates and specific surfaces, such as glass plates covered with silver particles or the like and microscopically roughened electrodes, and have dealt mainly with highly polarizable, small monocyclic molecules, such as pyridine and its derivatives, and with a few ionic species, such as the cyanide radical $CN^-$ and the anion of dithiozone. See A. Otto in 6 APPLICATIONS OF SURFACE SCIENCE 309-55 (North-Holland Publ. Co. 1980); Pemberton & Buck, 53 ANAL. CHEM. 2284 (1981) Vo-Dinh et al, 56 ANAL. CHEM. 1667 (1984), and references cited therein. As a consequence, no information on the reproducibility and general applicability of the SERS technique is available.

Furthermore, one of the greatest barriers to the analytical applications of SERS, especially for continuous monitors, is the lack of practical substrate materials that can be easily prepared and that can provide data with sufficient reproducibility and accuracy for analytical purposes. Heretofore, rigid surfaces were prepared for SERS via a variety of techniques, such as electrochemical roughening of electrode surfaces, lithographic etching, and the "prolade post" method. In the prolade post method, a $SiO_2$ support was first coated with a thin (4 to 5 nm) layer of etch-resistant metal, such as silver or aluminum, and the resulting metal layer was then disrupted by heating to form metal "islands" on the $SiO_2$ surface. Thereafter, the substrate was exposed to an $SiO_2$-etching plasma, so that surface areas between the metal islands were etched to produce metal-capped "posts." After the metal caps were removed by a acid wash, a SERS-active metal was deposited, e.g., by thermal evaporation, onto the ends of the posts to produce the SERS substrate. This approach is elaborate and time-consuming.

SUMMARY OF THE INVENTION

It is therefore an object of the present invention to provide a practical and efficient SERS-active substrate that can be easily prepared, is inexpensive, and gives reproducible results.

It is another object of the present invention to provide a flexible substrate material that permits the extension of SERS analytical capabilities to include trace organic analysis.

It is yet another object of the present invention to provide SERS apparatus utilizing the aforesaid flexible substrate for rapid, accurate detection and continuous measurement of organic compounds present in trace (subnanogram) quantities.

In accomplishing the foregoing objects, there has been provided, in accordance with one aspect of the present invention, a substrate for surface-enhanced Raman spectroscopy, comprising a flexible support having at least one SERS-active surface which carries (a) a coating comprised of microbodies, the coating being immediately adjacent to the surface; and (b) a metallized outer layer. In a preferred embodiment, the aforesaid substrate is the product of a process comprising the steps of coating the surface of the flexible substrate with an aqueous suspension of the above-mentioned microbodies, then spinning the substrate to effect a substantially even distribution of the microbodies across the surface; after the spinning step, drying the substrate surface; and thereafter depositing a metallic layer onto the surface coated with the microscopic bodies.

In accordance with another aspect of the present invention, there has been provided spectroscopy apparatus comprising (a) a laser excitation source; (b) a substrate as described above; (c) means for exposing a predetermined portion of the SERS-active surface to the source; (d) means for positioning the portion of the SERS-active surface in a predetermined relation to the source; and (e) spectrometric means for detecting a surface Raman signal from the portion of the SERS-active surface. In a preferred embodiment, the substrate comprises a tape which is advanced through the apparatus.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
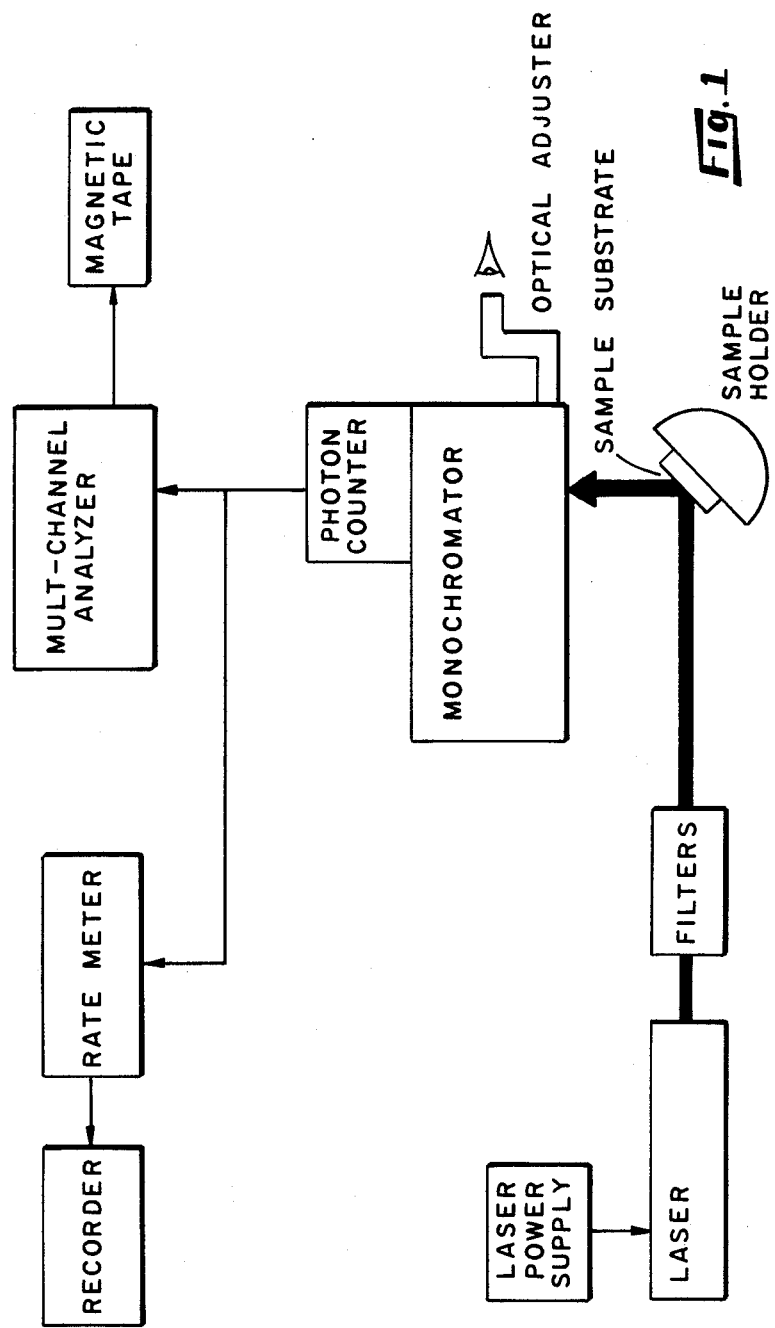
FIGS. 1 and 2 are schematic representations of apparatus within the present invention.

For the purposes of this description, a surface is characterized as "SERS-active" if it has the degree of roughness required to induce the SERS effect described above. In the present invention, the requisite surface roughness can be achieved by providing a support material, which is preferably flexible, e.g., cellulosic material like filter paper, with a coating of latex microspheres manufactured by Duke Scientific Corporation (Palo Alto, CA). The commercially available microspheres are made from polystyrene, polyvinyltoluene and polybutadiene, respectively, and are generally uniform in size and shape. However, beads in the submicron size range made from other materials, such as polytetrafluoroethylene (TEFLON ®), can be used in this context. Suitable TEFLON ® beads are manufactured by E. I. duPont de Nemours & Co. (Wilmington, DE). Also, nonspherical particles, such as platinum particles produced in accordance with Brugger et al, 103 J. AM. CHEM. SOC. 2923 (1981), and zirconium phosphate-base particles produced in accordance with Maya & Danis, 190 J. CHROMATOG. 145 (1980), as well as spherical bodies are suitable, so long as sufficient roughness is imparted thereby to the support surface. The term "microbodies" will be employed herein to refer to the class of roughness-imparting microspheres, submicron-sized beads, nonspherical particles and the like which are suitable for use in the present invention.

Preferably, microbodies applied to a substrate in accordance with the present invention are uniform in shape, and fall within the size range characteristic of the above-mentioned microspheres, i.e., between about 0.038 and 0.497 microns. As indicated above, the texture and degree of roughness of the substrate surface thus treated can be regulated, and the SERS effective optimized, by modifying the size of the microbodies used.

The support itself can be made from any material that can support a coating of microbodies and, in addition, a metallized overcoating, described in more detail below. Flexible support materials are preferred, especially for continuous monitors; for example, one or more optical fibers, plastic sheets, thin layer chromatographic (silica gel) sheets and thin metal sheets are suitable supports. Cellulosic support materials exemplified by filter paper (Whatman 50 or Millipore, e.g., 0.45 micron pore size) are especially preferred because of their relatively low cost and ready availability. Also, the surface protrusions and fibrous structure characteristic of cellulosic support material provide the advantages of added SERS effect-inducing roughness and increased surface area for sorption, respectively.

The microbodies can be applied in an aqueous suspension onto the support surface. To effect a uniform distribution of microbodies across the surface, as is preferred, the coated substrate can be spun in a conventional spinning device and then dried, preferably at room temperature. After drying, a metallized overcoating should be applied to the support, covering the microbodies previously provided. This can be accomplished by mounting the microbody coated substrate in the vacuum chamber of a conventional vacuum evaporator device and then depositing a layer of metal on the substrate. Alternatively, the overcoating metal can be sputtered onto the microbody-coated support surface, using known techniques.

The thickness of the metallized overcoating should be sufficient to cover the microbodies, so that a thicker overcoating is required when larger microbodies are used. Too thick a deposit can smoothen the substrate surface, decreasing the SERS effect; conversely, too thin a deposit may leave interstitial regions of the substrate uncoated with metal. In practice, the thickness of the metallized overcoating can be adjusted on a case-by-case basis to maximize Raman emissions from the SERS-active surface ("surface Raman signals"). Layer thicknesses of between about 100 and 2000 angstroms have been used.

A variety of metals can be used in the present invention, including gold, copper, tungsten and, to a lesser extent, platinum. Silver is preferred, however, for forming the metallized overcoating.

To use a substrate of the present invention in trace analysis, e.g., of organic molecules, the substrate must be exposed to a laser source such that the surface Raman signals can be detected, and the resulting Raman spectra employed, to characterize molecules previously sorbed at or (in cases where the sample is applied to the substrate in multiple layers) near the substrate surface. If the substrate is in the form of a plate or disk, e.g., of a suitable plastic material, a test sample can be applied to the SERS-active surface thereof by hand and the substrate positioned in a frame, as shown in FIG. 1, to permit precise irradiation of the substrate surface thus exposed to an excitation laser beam. The resulting surface Raman signals can be directed via a conventional optical system to a Raman spectrometer (see FIG. 1), where the spectra are then quantified and analyzed.

Figure 2:
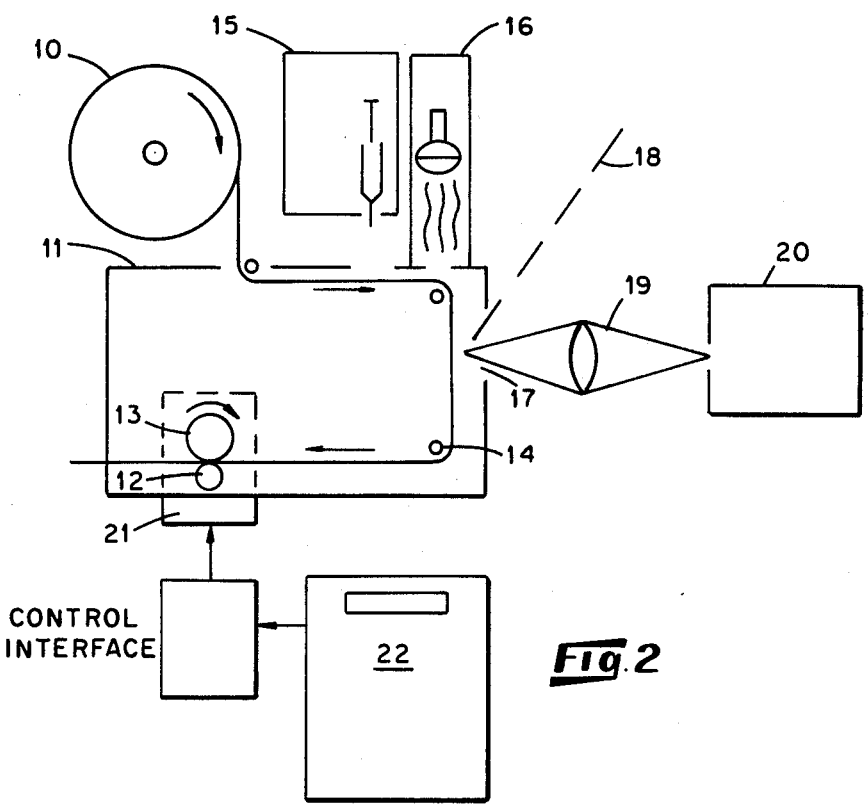

In a preferred embodiment of the present invention, a tape is supplied with an extended SERS-active surface and then drawn, preferably continuously, through apparatus as shown in FIG. 2. To produce such a tape, a ribbon of suitable support material is coated with microbodies (there being no spinning step) and then mounted on a cassette, such that only a portion of the ribbon is exposed at any given time. The cassette is sized to fit conveniently into the vacuum chamber of a conventional vacuum evaporator or sputtering device. Once mounted in a vacuum chamber, the cassette is advanced in such a way that successive portions of the microbody-coated surface are exposed and provided with the metallized overcoating, until the entire surface is rendered SERS-active. Alternatively, a plurality of substrates, each with a SERS-active surface, can be mounted in sequence on a tape which is drawn through the apparatus of FIG. 2.

With reference to FIG. 2, a tape-like carrier as described above, preferably comprising a cellulosic support material such as filter paper, is drawn from a roll 10 through a housing 11 by a stepping motor-driven roller 12 pressurized against a spring-loaded idler 13. The tape, with SERS-active surface outwardly exposed, follows a path, defined by a series of stationary guides 14, within the housing. A sample delivery unit 15 (an automated pipette or similar device) dispenses measured liquid test samples through a port in the top of the housing onto the SERS-active surface of the moving tape. A sample drying unit 16 provides heat from a heating lamp (or similar device) through a port in the housing to dry each passing sample on the tape. (For certain samples, e.g., those that are thermally sensitive, no heating step may be required.) Each sample is then moved past an excitation detection port 17, where the sample is exposed to a laser excitation source 18. The resulting surface Raman signals are collected and directed by a conventional optical system 19 to a Raman spectrometer 20. Sample delivery system 15 and a stepping motor 21 can be interfaced with a microcomputer 22 programmed to control the speed of the tape and the sample delivery interval, respectively.

Figure 3:
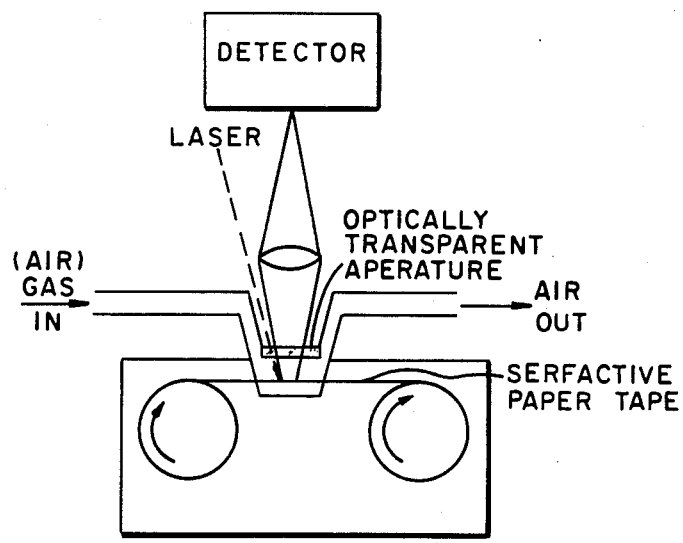
FIG. 3 is a schematic representation of a portion of apparatus modified from FIG. 2 to accommodate Raman spectrometric analysis of gaseous samples.

In another embodiment, shown in FIG. 3, apparatus of the present invention is equipped with a conduit to deliver a gaseous sample to the SERS-active surface of a tape-like substrate as described above. Molecular species contained in the carrier gas of the sample are sorbed onto the active surface and exposed to the laser source, generating characteristic Raman spectra.

EXAMPLE 1

Preparation of a substrate based on filter paper support

Figure 4:
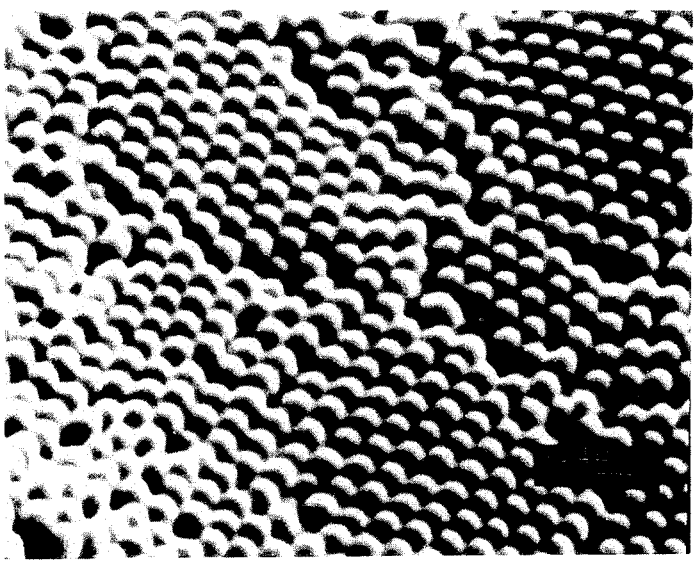
FIGS. 4, 5 and 6 are scanning electron microscope (SEM) photographs showing substrates before (FIG. 4) and after (FIGS. 5 and 6) the application of a metallized overcoating in accordance with the present invention.

An aqueous dispersion of 0.038 micron latex microspheres (10 wt.-% solids) manufactured by Duke Scientific Corp. (Palo Alto, CA) was diluted with distilled water in a ratio of approximately 1:10. About 100 μl of the diluted microsphere suspension was applied to a Whatman 50 filter paper support. The coated support was spun at 800–2000 rpm for approximately 20 seconds in a conventional rotating spinning device, and then was allowed to dry in air at room temperature. A scanning electron microscope (SEM) photograph of the resulting microsphere-bearing surface is shown in FIG. 4.

Figure 5:

After drying, the support was mounted on a holder inside a vacuum chamber (Thermionics Laboratory, Inc., Boston, MA) where silver was allowed to thermally evaporate onto the microsphere-bearing surface. The time for evaporation, the evaporation rate, and the silver coating thickness were precisely controlled via the thermal evaporation unit. The thickness of the silver deposit was measured with a Model QM311 quartz crystal thickness monitor (Kronos, Inc., Torrance, CA) to be approximately 1500 angstroms. A SEM photograph of the final substrate is shown in FIG. 5. (Note the distance scale at the lower right corner.) Because the ultimate resolution of the SEM is approximately 0.030 μm, the microspheres are too small to be seen. However, the fibrous structure of the paper support is plainly visible.

Figure 6:
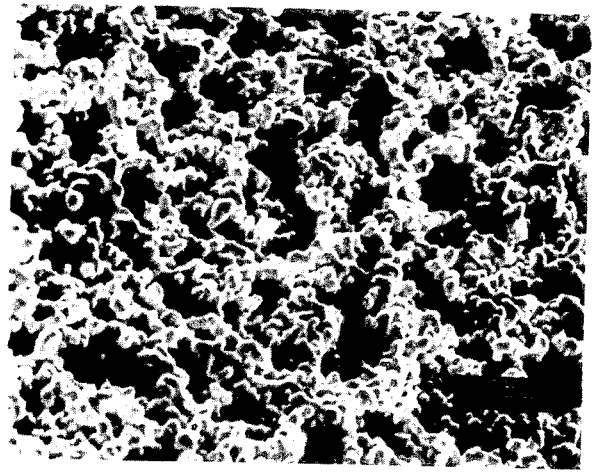

FIG. 6 shows an SEM photograph of Millipore paper coated with 0.497 micron microspheres and a 2000 angstrom overcoating of silver, following the same general procedure as described above but omitting the spinning step. The fibrous structure of the paper substrate increased the effective surface area available for the microspheres and for the sorbate molecules. Although the orientations of the paper fibers was not uniform, the diameter of the excitation laser beam can compensate for this nonuniformity, since the beam diameter is much larger than the surface roughness. (Typically, the laser beam diameter is over 20 times the width of FIG. 2.) As a consequence, the total number of microspheres illuminated by the laser is large enough to give a reproducible surface Raman signal.

EXAMPLE 2

Use of filter-base substrate for surface-enhanced Raman spectroscopy

Surface-enhanced Raman measurements were successfully conducted for several organic compounds, including benzoic acid, pyrene, acridine, carbazole, 1-nitropyrene and 1-aminopyrene. Benzoic acid was selected as the model compound for detailed investigation because the Raman spectrum of this compound has been previously investigated. The substrates used for these measurements were prepared by the procedure described above, using Whatman 50 filter paper as the support, 0.091 micron microspheres, and a 2000 angstrom-thick overcoating of silver. The substrates were each mounted in a sample holder of an apparatus as shown in FIG. 1.

Figure 7:
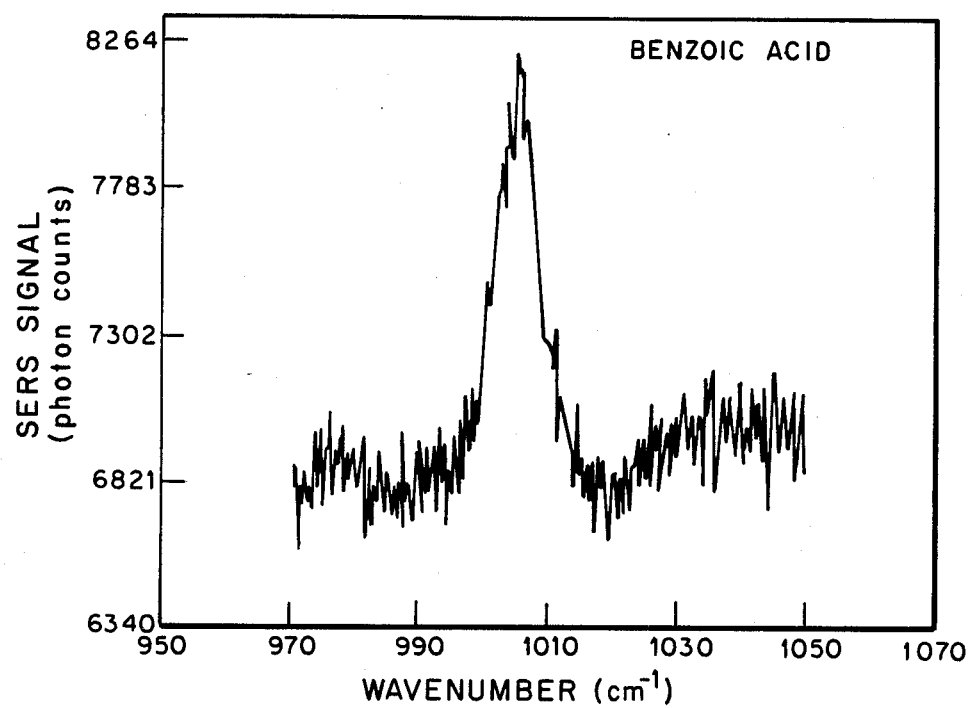
FIG. 7 is a graph showing the Raman emission spectrum of a 3.6 ng sample of benzoic acid applied to a substrate of the present invention.

Samples of the test compounds were added to the substrates by spotting a 3 μl aliquot of an ethanolic solution ($10^{-6}$M) of the compound onto the substrate. FIG. 7 shows an example of the detection of 3.6 ng benzoic acid sorbed onto the SERS-active surface of the substrate. The laser used had a power of 50 mW and an excitation wavelength of 514.5 nm. The optical limit of detection for benzoic acid was 0.3 ng. The signal accumulation time per data point was only 100 milliseconds. The detection limits per sample spot for most of the other compounds investigated were in the nanogram and subnanogram levels: carbazole (0.2 ng) at 1061 cm$^{-1}$ and 1-aminopyrene (1.4 ng) at 1185 cm$^{-1}$. It should be emphasized that these limits of detection are given per sample spot and, hence, do not account for the laser/sample illumination ratio. Since the sample area actually illuminated by the laser beam was only 1/100 of the total sample spot, the actual limits of detection are only 36 pg, 2 pg and 14 pg for p-aminobenzoic acid, carbazole and 1-aminopyrene, respectively.

Figure 8:
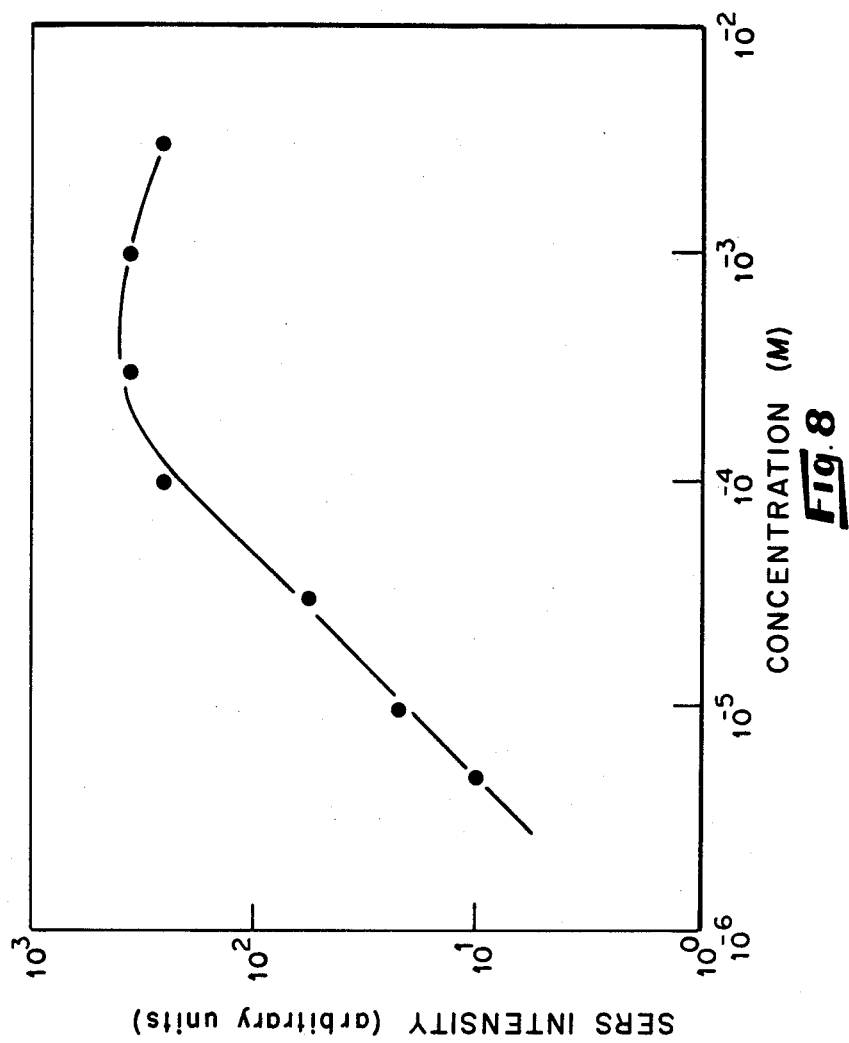
FIG. 8 is a graph showing the results of trace analyses of 1-aminopyrene, obtained using substrate and apparatus within the present invention.

A typical analytical curve of 1-aminopyrene obtained in accordance with the above-described protocol is illustrated in FIG. 8. The data were obtained with the 1185 cm$^{-1}$ Raman band, using a 633 nm laser excitation. The slope of the log-log analytical curve is close to unity over two orders of magnitude. Measurements performed with benzoic acid and carbazole showed that the calibration curve is linear from $10^{-3}$M to $10^{-6}$M and $10^{-7}$M, respectively. Saturation effects apparently occurred above $10^{-3}$M as the surface Raman signal-concentration curves tended to be nonlinear beyond this concentration. Results of multiple measurements conducted on samples identically prepared gave a relative standard deviation of 15–20%. This reproducibility would be quite satisfactory for most analytical studies.

EXAMPLE 3

Performance of continuous apparatus using fiber-base substrate

Figure 9:
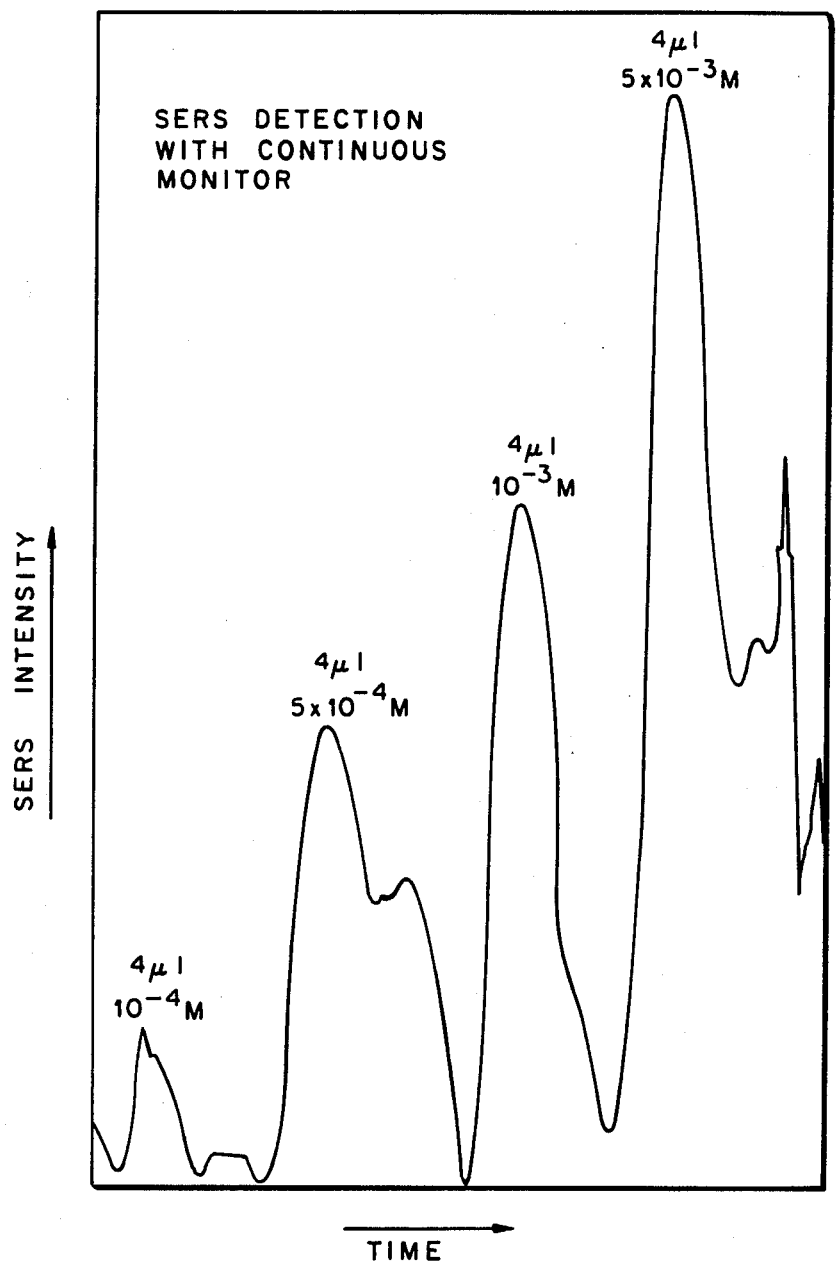
FIG. 9 is a graph showing results of continuous, sequential Raman-spectrometric analyses conducted on four samples comprising differing concentrations of 1-nitropyrene.

A series of samples was analyzed in sequence wih a continuous monitor device as shown in FIG. 2 in order to demonstrate the feasability of continuous SERS monitoring, as well as the speed and detection accuracy of apparatus within the present invention. The samples were solutions having a volume of 4 μl each and containing, respectively, concentrations of 1-nitropyrene of $10^{-4}$M, $5\times10^{-4}$M, $10^{-3}$M and $5\times10^{-3}$M. Each sample was applied to a separate substrate comprised of Whatman 50 filter paper, a coating thereon of 0.038 μm polystyrene latex microspheres, and a silver metal overcoating. Each substrate was mounted on a paper carrier tape, as described above, and run in sequence through apparatus as shown in FIG. 2. The results of these tests are shown in FIG. 9.

The substrate of the present invention will find wide application in SERS-based analyses for trace amounts of organic compounds. Apparatus within the present invention can be adapted for use as continuous field monitors of energy-related pollutants, toxic chemicals, indoor and outdoor air pollutants, and other hazardous substances encountered in the environment.

What is claimed is:

1. A substrate for surface-enhanced Raman spectroscopy, comprising:
   (a) a flexible support, said support having at least one SERS-active surface;
   (b) a coating on said surface comprised of microbodies, said coating being immediately adjacent to said surface; and
   (c) a metallized outer layer.

2. A substrate according to claim 1, said substrate being the product of a process comprising the steps of
   (a) coating said surface of said substrate with an aqueous suspension of said microbodies; then
   (b) drying said surface; and thereafter
   (c) depositing a metallic layer onto said surface coated with said microbodies.

3. A substrate according to claim 2, further comprising after step (a) the step of spinning said substrate to effect a substantially even distribution of said microbodies across said surface.

4. A substrate according to claim 2, wherein step (c) comprises thermally evaporating a metal selected from the group consisting of silver, gold, copper, tungsten and platinum under vacuum onto said microbodies.

5. A substrate according to claim 4, wherein said metal is silver.

6. A substrate according to claim 1, wherein said support comprises a cellulosic material.

7. A substrate according to claim 6, wherein said cellulosic material is filter paper.

8. A substrate according to claim 1, wherein said support comprises at least one optical fiber.

9. A substrate according to claim 1, wherein said microbodies comprise at least one material from the group consisting of polytetrafluoroethylene, polystyrene, polyvinyltoluene and polybutadiene.

10. A substrate according to claim 9, wherein said microbodies comprise polystyrene latex microspheres.

11. A substrate according to claim 1, wherein said microbodies comprise at least one material from the group consisting of platinum and zirconium phosphate.

12. A substrate according to claim 1, wherein said microbodies range in size from about 0.038 and 0.497 microns.

13. Spectroscopy apparatus comprising
   (a) a laser excitation source;
   (b) a substrate for surface-enhanced Raman spectroscopy, said substrate comprising (i) a flexible support having at least one SERS-active surface, (ii) a coating on said surface comprised of microbodies, said coating being immediately adjacent to said surface, and (iii) a metallized outer layer;
   (c) means for exposing a predetermined portion of said SERS-active surface to said source;
   (d) means for positioning said portion of said SERS-active surface in a predetermined relation to said source;
   (e) spectrometric means for detecting a surface Raman signal from said portion of said SERS-active surface.

14. Apparatus according to claim 13, further comprising means for delivering a test sample to said portion of said SERS-active surface.

15. Apparatus according to claim 13, wherein said substrate comprises a tape, and said means (d) comprises means for advancing said tape through said apparatus.

16. Apparatus according to claim 15, wherein said means for advancing said tape comprises a stepping motor-driven roller for drawing said tape through said apparatus, said roller being in pressurized contact with a spring-loaded idler.

17. Apparatus according to claim 14, wherein said means for delivering comprises a conduit for delivering a gaseous test sample to said portion of said SERS-active surface.

18. Apparatus according to claim 14, wherein means for delivering comprises means for pipetting a predetermined volume of a liquid test sample onto said portion of said SERS-active surface.

19. Apparatus according to claim 18, further comprising means for drying said portion of said SERS-active surface after said volume of a liquid sample has been pipetted onto said portion.

* * * * *